(12) United States Patent
Hoshino et al.

(10) Patent No.: US 10,464,284 B2
(45) Date of Patent: Nov. 5, 2019

(54) NON-INTERFERING TESTING MEMBER INCLUDING A THERMOPLASTIC RESIN LAYER

(71) Applicant: LINTEC CORPORATION, Tokyo (JP)

(72) Inventors: Hiroki Hoshino, Tokyo (JP); Masaya Todaka, Tokyo (JP); Tomoo Orui, Tokyo (JP)

(73) Assignee: LINTEC CORPORATION, Tokyo (JP)

( * ) Notice: Subject to any disclaimer, the term of this patent is extended or adjusted under 35 U.S.C. 154(b) by 0 days.

(21) Appl. No.: 15/832,914

(22) Filed: Dec. 6, 2017

(65) Prior Publication Data

US 2018/0178485 A1    Jun. 28, 2018

(30) Foreign Application Priority Data

Dec. 22, 2016    (JP) .................. 2016-250108

(51) Int. Cl.
*B32B 3/30* (2006.01)
*B32B 27/06* (2006.01)
(Continued)

(52) U.S. Cl.
CPC ............ *B32B 3/30* (2013.01); *B32B 27/06* (2013.01); *B32B 37/06* (2013.01); *G01N 21/03* (2013.01);
(Continued)

(58) Field of Classification Search
CPC ........... B32B 3/30; B32B 27/06; B32B 37/06; B32B 2307/412; B32B 2309/105;
(Continued)

(56) References Cited

U.S. PATENT DOCUMENTS

| 4,761,381 A * | 8/1988 | Blatt ................. B01L 3/502738 356/246 |
| 2004/0197231 A1* | 10/2004 | Katsuki .............. A61B 5/14532 422/68.1 |

(Continued)

FOREIGN PATENT DOCUMENTS

| JP | 2006-510384 A | 3/2006 |
| JP | 2008-157644 A | 7/2008 |

(Continued)

OTHER PUBLICATIONS

Misumi, Plastic Molding Tutorial, Feb. 29, 2012, waybackmachine, https://web.archive.org/web/20120229133959/http://www.misumi-techcentral.com/tt/en/mold/2011/12/106-glass-transition-temperature-tg-of-plastics.html (Year: 2012).*

*Primary Examiner* — Michael P LaPage
(74) *Attorney, Agent, or Firm* — Posz Law Group, PLC

(57) ABSTRACT

[Problems] Objects include providing a cover film for testing that can be well fixed to a substrate having a groove and does not adversely affect the groove, providing a testing member comprising the cover film for testing, and providing a method of manufacturing the testing member.

[Solution] The cover film for testing (1) comprises a base material (10) and a thermoplastic resin layer (20) laminated on one surface side of the base material (10). The thermoplastic resin layer (20) constitutes an outermost layer at one side of the cover film for testing (1).

7 Claims, 1 Drawing Sheet

(51) Int. Cl.
*B32B 37/06* (2006.01)
*G01N 21/03* (2006.01)
*G01N 21/51* (2006.01)
*G01N 21/64* (2006.01)

(52) U.S. Cl.
CPC ... *B32B 2307/412* (2013.01); *B32B 2309/105* (2013.01); *G01N 21/51* (2013.01); *G01N 2021/0357* (2013.01); *G01N 2021/0378* (2013.01); *G01N 2021/6482* (2013.01)

(58) Field of Classification Search
CPC ........... G01N 2021/6482; G01N 21/51; G01N 2021/0378; G01N 2021/0357; G01N 21/03–21/07
See application file for complete search history.

(56) References Cited

U.S. PATENT DOCUMENTS

2012/0266985 A1* 10/2012 Momose ............. B29C 65/1435
                                                        137/561 R
2016/0279639 A1*  9/2016 Kim ....................... B01L 7/525

FOREIGN PATENT DOCUMENTS

| WO | 2004/058405 A1 | 7/2004 |
| WO | 2012/056878 A1 | 5/2012 |

\* cited by examiner

NON-INTERFERING TESTING MEMBER INCLUDING A THERMOPLASTIC RESIN LAYER

TECHNICAL FIELD

The present invention relates to a testing member used for optically testing a specimen, a cover film for testing used in the testing member, and a method of manufacturing the testing member.

BACKGROUND ART

A method of optically testing a specimen exists for the purpose of measuring the turbidity of a specimen such as liquid, the amount of a specific component in the specimen, and other items. In such an optical testing method, the specimen is irradiated with light to measure light that is caused by the irradiation. More specific examples of such a testing method include a method of irradiating a specimen with light and measuring the degree of scattering of the light, a method of measuring an amount of absorption of light by a component in a specimen when the specimen is irradiated with light and the light transmits through the specimen, and a method of measuring fluorescence caused in a specimen. In such a testing method, conventionally, the specimen has been stored in a test tube or cell having an appropriate volume, such as several milliliters.

In recent years, a testing method is developed which uses a testing member provided with a fine groove for storing a specimen, as substitute for the above test tube or cell. In such a method, the test is possible even for a small amount of the specimen and thus requires only a slight amount of the specimen. Moreover, the use of a testing member having a plurality of grooves enables collective measurement and a number of specimens can therefore be tested at the same time.

Patent Literature 1 discloses a multi-layered composite structure as an example of the above-described testing member having fine grooves. The multi-layered composite structure comprises a base material that constitutes side surfaces of the grooves, a first layer that constitutes bottom surfaces of the grooves, and a resealable film as a cover that covers the grooves (paragraph 0032 and FIG. 2 of Patent Literature 1). Patent Literature 2 discloses a plastic microchip in which a plastic substrate that has a fine flow channel as the above groove at the surface and a plastic film as a cover that covers the groove are bonded together via an adhesive (claim 1 of Patent Literature 2). Patent Literature 3 discloses a microchip obtained by thermal bonding between a resin substrate that has grooves for flow channels on the surface and a resin cover member that covers the grooves for flow channels and also discloses that the resin substrate and the resin cover member are formed of polycarbonate resin (claim 1 and paragraph 0065 of Patent Literature 3).

PRIOR ART LITERATURE

Patent Literature

[Patent Literature 1] Japanese Translation of PCT International Application, No. 2006-510384
[Patent Literature 2] JP2008-157644A
[Patent Literature 3] WO2012/056878

SUMMARY OF THE INVENTION

Problems to be Solved by the Invention

As installed in the testing members described in Patent Literature 1 to 3, the grooves may be covered by a cover to prevent troubles, such as vaporization and leakage of specimens and pollution of specimens. Such a cover has to be well fixed to the substrate in order to prevent its delamination and dropping from the substrate provided with the grooves. Such a cover may therefore be fixed to the substrate using an adhesive or pressure sensitive adhesive.

For example, in Patent Literature 2, the plastic film is adhered using an adhesive to the surface of the plastic substrate having the fine flow channel. In the fixing method as disclosed in Patent Literature 2, however, the adhesive or pressure sensitive adhesive used may invade into the groove and/or fill the groove. In this case, the test cannot be well performed because the specimen cannot be sufficiently stored in the groove.

In the microchip as disclosed in Patent Literature 3, the resin substrate and the resin cover member are thermally bonded together. Specifically, Patent Literature 3 discloses an example in which the resin substrate and the resin cover member are bonded together by thermocompression. In the fixing method as disclosed in Patent Literature 3, however, the resin substrate has to be heated to a temperature beyond the melting start temperature of the resin which constitutes the resin substrate. Thus, the test may not be well performed because the grooves for flow channels existing at the surface of the resin substrate may deform due to heat.

The present invention has been made in consideration of such actual circumstances and an object of the present invention is to provide a cover film for testing that can be well fixed to a substrate having a groove and does not adversely affect the groove. Another object of the present invention is to provide a testing member comprising the cover film for testing. A further object of the present invention is to provide a method of manufacturing the testing member.

Means for Solving the Problems

To achieve the above objects, first, the present invention provides a cover film for testing comprising: a base material: and a thermoplastic resin layer laminated on one surface side of the base material, the thermoplastic resin layer constituting an outermost layer at one side of the cover film for testing (Invention 1).

The cover film for testing according to the above invention (Invention 1) includes the thermoplastic resin layer and, therefore, the cover film for testing and a substrate can be well fixed to each other by thermal fusion bonding of the thermoplastic resin layer. This fixation does not require heating the substrate to its melting temperature. A groove of the substrate can thus be prevented from deforming due to heat. Moreover, the thermoplastic resin is suppressed from invading into the groove of the substrate because the thermoplastic resin has high elasticity even during the thermal fusion bonding as compared with a pressure sensitive adhesive. As a result of these, the use of the cover film for testing allows a testing member to be obtained with which the test can be well performed.

In the above invention (Invention 1), a thermoplastic resin that constitutes the thermoplastic resin layer may preferably have a glass-transition temperature (Tg) of 35° C. or higher and 150° C. or lower (Invention 2).

In the above invention (Invention 1), the cover film for testing may preferably have a thickness of 30.5 μm or more and 330 μm or less (Invention 3).

Second, the present invention provides a testing member comprising: a substrate having a surface provided with at least one groove; and a cover film laminated on the surface of the substrate provided with the groove, the cover film being the above cover film for testing (Invention 1), the testing member being for performing an optical test for a specimen stored in the groove (Invention 4).

In the above invention (Invention 4), the cover film for testing may preferably have transparency to light used in the test (Invention 5).

In the above invention (Invention 4), the substrate may preferably have transparency to light used in the test (Invention 6).

Third, the present invention provides a method of manufacturing the above testing member (Invention 4), the method comprising a step of performing thermal fusion bonding between the surface of the substrate provided with the groove and a surface of the cover film for testing at the thermoplastic resin layer side so that the substrate and the cover film for testing adhere to each other, the thermal fusion bonding being performed without filling the groove with the thermoplastic resin layer (Invention 7).

Advantageous Effect of the Invention

The cover film for testing of the present invention can be well fixed to the substrate having the groove and the groove is not adversely affected because the thermoplastic resin is suppressed from invading into the groove and the groove does not deform due to heat. Moreover, according to the cover film for testing of the present invention, the test can be well performed. Furthermore, according to the method of manufacturing of the present invention, the testing member as the above can be manufactured.

EMBODIMENTS FOR CARRYING OUT THE INVENTION

Figure 1:
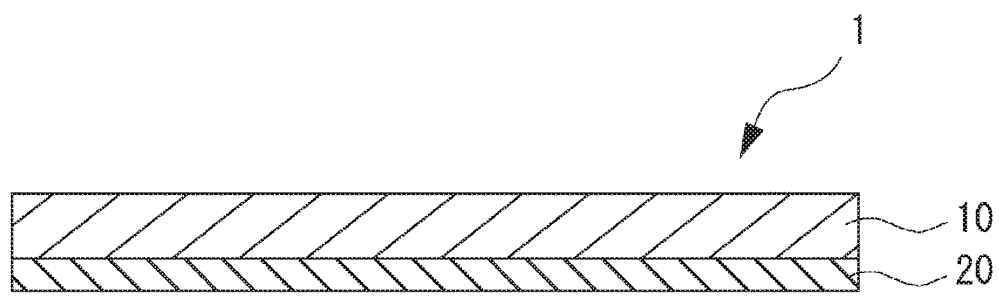
FIG. 1 is a cross-sectional view of a cover film for testing according to an embodiment of the present invention.

Hereinafter, embodiments of the present invention will be described.
<Cover Film for Testing>
FIG. 1 illustrates a cover film for testing 1 according to the present embodiment. The cover film for testing 1 comprises a base material 10 and a thermoplastic resin layer 20 that is laminated entirely on one surface side of the base material 10. In the cover film for testing 1 according to the present embodiment, the thermoplastic resin layer 20 constitutes the outermost layer at one side of the cover film for testing 1.

Figure 2:
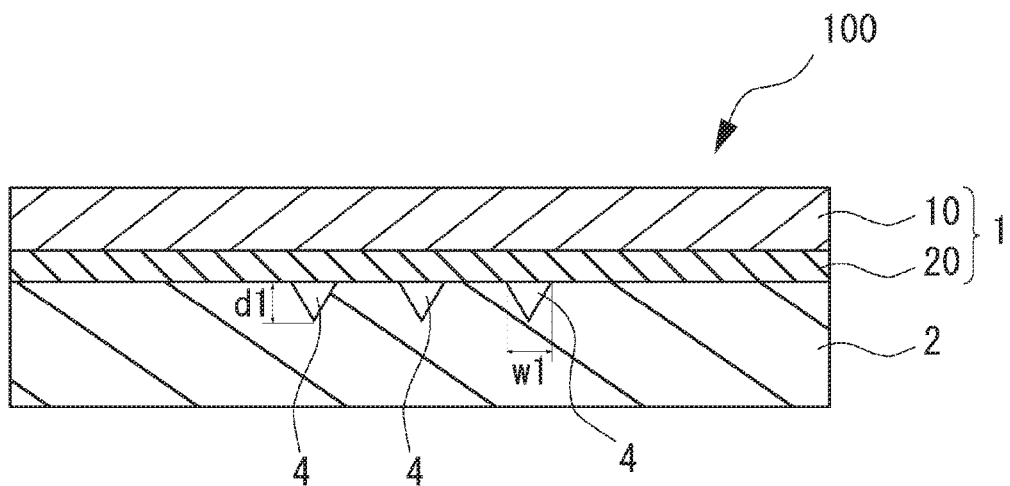
FIG. 2 is a cross-sectional view of a testing member according to an embodiment of the present invention.

The cover film for testing 1 according to the present embodiment may be for constituting a testing member used in a test and may preferably be for constituting a testing member 100 as illustrated in FIG. 2. The testing member 100 comprises a substrate 2 having a surface provided with at least one groove 4 and the cover film for testing 1 laminated on the surface of the substrate 2 provided with the grooves 4 and may be for performing an optical test for a specimen stored in each groove 4. When the cover film for testing 1 according to the present embodiment is used to constitute the testing member 100, the thermoplastic resin layer 20 is used to attach the substrate 2 and the base material 10 to each other.

The cover film for testing 1 according to the present embodiment includes the thermoplastic resin layer 20, which can well fix the cover film for testing 1 and the substrate 2 by heating the thermoplastic resin layer 20 into a molten state and then laminating the cover film for testing 1 and the substrate 2. The cover film for testing 1 and the substrate 2 can thus be fixed to each other without using a pressure sensitive adhesive which might invade into the grooves 4 of the substrate 2. Moreover, the grooves 4 of the substrate 2 can be suppressed from deforming due to heat because the fixation through such thermal fusion bonding of the thermoplastic resin layer 20 can be achieved without heating the substrate 2 to its melting temperature. Furthermore, the thermoplastic resin which constitutes the thermoplastic resin layer 20 has high elasticity even when heated as compared with a pressure sensitive adhesive and, therefore, the thermoplastic resin can also be suppressed from invading into the grooves 4 when laminated on the substrate 2 in the molten state. As the above, the cover film for testing 1 according to the present embodiment does not adversely affect the grooves 4 of the substrate 2 and can be well fixed to the substrate 2. The testing member 100 is thus obtained with which the test can be well performed.

In the fixation between the cover film for testing 1 according to the present embodiment and the substrate 2, it suffices that the thermoplastic resin layer 20 in a molten state due to heating can be laminated on the substrate 2, and the specific scheme is not limited. For example, a simple scheme can be selected, such as thermal lamination using heating rollers. Moreover, a scheme of highly safe workability can be selected because the substrate 2 is not required to be heated to a temperature beyond its melting point.

1. Configuration of Cover Film for Testing
(1) Base Material

In the cover film for testing 1 according to the present embodiment, the configuration of the base material 10 is not particularly limited, provided that the test can be performed using the testing member 100 which includes the base material 10. From the viewpoint of enabling a good test, it may be preferred for the base material 10 to have transparency to light used in the test (which may be referred to "testing light," hereinafter) and have optical isotropy.

As a material of the base material 10, a resin film, glass, and other appropriate material can be used, among which the resin film may preferably be used from the viewpoint of easy production and easy handling. Examples of the resin film include a polycarbonate film, films of polyester, such as polyethylene terephthalate, polybutylene terephthalate and polyethylene naphthalate, films of polyolefin, such as polyethylene and polypropylene, cellophane, a diacetyl cellulose film, triacetyl cellulose film, acetyl cellulose butyrate film, polyvinyl chloride film, polyvinylidene chloride film, polyvinyl alcohol film, ethylene-vinyl acetate copolymer film, polystyrene film, polymethylpentene film, polysulfone film, polyether ether ketone film, polyether sulfone film, polyetherimide film, polyimide film, fluorine resin film, polyamide film, acrylic resin film, norbornene-based resin film, cycloolefin resin film, polyphenylene sulfide film, and liquid-crystal polymer film. These films may be in a single layer or may also be in a multilayer obtained by laminating two or more layers of the same type or different types.

The above resin film may preferably be an unstretched film from the viewpoint of optical isotropy. Among the above resin films, the polycarbonate film, polyethylene terephthalate film, polybutylene terephthalate film, cycloolefin resin film, or acrylic resin film may preferably be used and the polycarbonate film may be particularly preferably used from the viewpoint of excellent transparency to the testing light. Details of the testing light will be described later.

The same material as that of the substrate 2 may preferably be used as a material of the base material 10. The use of the same material can reduce the difference in the transparency to the testing light between the base material 10 and the substrate 2 and the influence of such a difference on the measurement can be reduced.

In the cover film for testing 1 according to the present embodiment, the transmittance of the testing light through the base material 10 may be preferably 60% or higher, particularly preferably 80% or higher, and further preferably 90% or higher. The above transmittance being 60% or higher allows the cover film for testing 1 to have better transparency to the testing light. As a result, in the testing member 100 obtained using the cover film for testing 1, the testing can be more accurately performed. The upper limit of the above transmittance is not particularly limited and may be 100% or lower.

In the cover film for testing 1 according to the present embodiment, the haze value of the base material 10 may be preferably 10% or less, particularly preferably 5% or less, and further preferably 1% or less. The haze value of the base material 10 being 10% or less can effectively reduce the scattering of the testing light in the base material 10. In the testing member 100 obtained using the cover film for testing 1, therefore, the testing can be more accurately performed. The lower limit of the haze value of the base material 10 is not particularly limited, but may ordinarily be 0% or more. The haze value as used in the present description refers to a value that is measured in accordance with JIS K7136: 2000.

For the purpose of improving the interfacial adhesion of the base material 10 with the thermoplastic resin layer 20, the base material 10 can be subjected to surface treatment, such as using an oxidation method and roughening method, or primer treatment, provided that the transparency to the testing light is not impaired. Examples of the above oxidation method include corona discharge treatment, plasma discharge treatment, chromium oxidation treatment (wet type), flame treatment, hot-air treatment, ozone exposure treatment, and ultraviolet ray irradiation treatment. Examples of the roughening method include a sandblast method and thermal spraying method. These surface treatment methods may be appropriately selected in accordance with the type of the material which constitutes the base material 10.

The glass-transition temperature (Tg) of the material which constitutes the base material 10 may be preferably 100° C. or higher, particularly preferably 120° C. or higher, and further preferably 140° C. or higher. When the above glass-transition temperature (Tg) is 100° C. or higher, the base material 10 does not readily melt even if the testing member 100 is heated during the test. It is therefore possible to effectively suppress the deformation of the base material 10 and to effectively suppress the occurrence of delamination and/or displacement at the interface between the base material 10 and the thermoplastic resin layer 20. The upper limit of the glass-transition temperature (Tg) of the material which constitutes the base material 10 is not particularly restricted, but in general may be preferably 300° C. or lower, particularly preferably 250° C. or lower, and further preferably 200° C. or lower.

The thickness of the base material 10 may be preferably 30 µm or more, particularly preferably 50 µm or more, further preferably 75 µm or more, and most preferably 90 µm or more. The thickness may be preferably 300 µm or less, particularly preferably 200 µm or less, further preferably 150 µm or less, and most preferably 110 µm or less. The thickness of the base material 10 being 30 µm or more allows the base material 10 to have sufficient strength to improve the handling ability and it is possible to suppress the deformation and breakage of the base material 10 when the testing member 100 is used. The thickness of the base material 10 being 300 µm or less allows the base material 10 to readily have excellent transparency to the testing light and the test may be well performed in the obtained testing member 100.

(2) Thermoplastic Resin Layer

In the cover film for testing 1 according to the present embodiment, the thermoplastic resin which constitutes the thermoplastic resin layer 20 is not particularly limited, provided that the thermoplastic resin can well fix the cover film for testing 1 and the substrate 2 by thermal fusion bonding and does not adversely affect the test.

Specific examples of the above thermoplastic resin include a polyolefin-based resin, polyester-based resin, polyurethane-based resin, polyester urethane-based resin, acrylic-based resin, amide-based resin, styrene-based resin, silane-based resin, and rubber-based resin. The polyolefin-based resin may be modified. Examples of the modified polyolefin-based resin include an acid-modified polyolefin-based resin and silane-modified polyolefin-based resin. On type of them may be solely used or a mixture of two or more types may also be used.

Examples of the polyolefin-based resin (unmodified polyolefin-based resin) include polyethylene resin, such as very low density polyethylene (VLDPE, density: 880 kg/m$^3$ or more and less than 910 kg/m$^3$), low density polyethylene (LDPE, density: 910 kg/m$^3$ or more and less than 915 kg/m$^3$), middle density polyethylene (MDPE, density: 915 kg/m$^3$ or more and less than 942 kg/m$^3$) and high density polyethylene (HDPE, density: 942 kg/m$^3$ or more), polypropylene resin (PP), ethylene-propylene copolymer, olefin-based elastomer (TPO), ethylene-vinyl acetate copolymer (EVA), ethylene-vinyl acetate-maleic anhydride copolymer, ethylene-(meth)acrylic acid copolymer, ethylene-(meth)acrylic ester copolymer, and ethylene-(meth)acrylic ester-maleic anhydride copolymer. As used in the present description, the ethylene-(meth)acrylic acid copolymer refers to both ethylene-acrylic acid copolymer and ethylene-methacrylic acid copolymer. The same applies to other similar terms.

The thermoplastic resin may also be an ionomer in which molecules are bonded by metal cations. Examples of the ionomer include an olefin-based ionomer, urethane-based ionomer, styrene-based ionomer, and fluorine-based ionomer. One type of ionomer may be solely used or a mixture of two or more types may also be used.

Among the above specific examples of the thermoplastic resin, the polyolefin-based resin, polyester-based resin, or acrylic-based resin may be preferred and the polyester-based resin may be particularly preferred from the viewpoint of exhibiting good interfacial adhesion and from the viewpoint that the thermoplastic resin is less likely to adversely affect the test using the testing member 100.

The glass-transition temperature (Tg) of the thermoplastic resin which constitutes the thermoplastic resin layer 20 may be preferably 35° C. or higher, particularly preferably 40° C. or higher, and further preferably 45° C. or higher. The glass-transition temperature (Tg) may be preferably 150° C. or lower, particularly preferably 145° C. or lower, and further preferably 140° C. or lower. When the above glass-transition temperature (Tg) is 35° C. or higher, the thermoplastic resin layer 20 does not readily melt even if the testing member 100 is heated during the test. It is therefore possible to effectively suppress the occurrence of delamination and/or displacement at the interface between the thermoplastic resin layer 20 and the base material 10 or the substrate 2. When the above glass-transition temperature (Tg) is 150° C. or lower, excessive heating is not necessary for the production of the testing member 100 during the fixation of the cover film for testing 1 and the substrate 2 by thermal fusion bonding of the thermoplastic resin layer 20. It is therefore possible to prevent the deformation of other members and reduce the production cost.

The thickness of the thermoplastic resin layer 20 may be preferably 0.5 µm or more, particularly preferably 0.8 µm or more, and further preferably 1 µm or more. The thickness may be preferably 30 µm or less, particularly preferably 20 µm or less, further preferably 10 µm or less, and most preferably 4 µm or less. The thickness of the thermoplastic resin layer 20 being 0.5 µm or more allows the cover film for testing 1 to be well fixed to the substrate 2. The thickness of the thermoplastic resin layer 20 being 30 µm or less can reduce the influence on the test due to the thickness of the thermoplastic resin layer 20 and the test may be well performed in the obtained testing member 100.

2. Physical Properties of Cover Film for Testing

The cover film for testing 1 according to the present embodiment may preferably have transparency to the light used in the test. This allows the testing light to well transmit through the cover film for testing 1 when performing the test using the testing member 100 which includes the cover film for testing 1. As a result, the testing member 100 can have improved accuracy in the test.

The transmittance of the testing light through the cover film for testing 1 according to the present embodiment may be preferably 60% or higher, particularly preferably 80% or higher, and further preferably 90% or higher. The above transmittance being 60% or higher allows the cover film for testing 1 to have better transparency to the testing light. As a result, in the testing member 100 obtained using the cover film for testing 1, the test can be more accurately performed. The upper limit of the above transmittance is not particularly limited and may be 100% or lower.

The haze value of the cover film for testing 1 according to the present embodiment may be preferably 10% or less, particularly preferably 5% or less, and further preferably 1% or less. The haze value being 10% or less can effectively reduce the scattering of the testing light in the cover film for testing 1. In the testing member 100 obtained using the cover film for testing 1, therefore, the test can be more accurately performed. The lower limit of the haze value of the cover film for testing 1 is not particularly limited, but may ordinarily be 0% or more.

In the cover film for testing 1 according to the present embodiment, the arithmetic average roughness (Ra) of the surface of the base material 10 opposite to the thermoplastic resin layer 20 may be preferably 200 nm or less, particularly preferably 100 nm or less, and further preferably 50 nm or less. The arithmetic average roughness (Ra) being 200 nm or less can suppress the diffuse reflection of the testing light at the surface of the cover film for testing 1 at the base material 10 side and the cover film for testing 1 may readily have excellent transparency to the testing light. As a result, the obtained testing member 100 can have improved accuracy in the test. The lower limit of the above arithmetic average roughness (Ra) is not particularly limited, but in general may be preferably 0.1 nm or more, particularly preferably 0.5 nm or more, and further preferably 1 nm or more.

The arithmetic average roughness (Ra) of the surface of the base material 10 opposite to the thermoplastic resin layer 20 can be obtained through fixing the cover film for testing 1 to a glass plate via a double-sided tape so that the surface of the cover film for testing 1 at the thermoplastic resin layer 20 side is located at the glass plate side and then performing measurement on the surface of the cover film for testing 1 at the base material 10 side using a surface roughness meter (product name "rSV-3000S4" available from Mitutoyo Corporation, stylus type) in accordance with JIS B0601: 2013.

The thickness of the cover film for testing 1 according to the present embodiment may be preferably 30.5 µm or more, particularly preferably 50.8 µm or more, and further preferably 76 µm or more. The thickness may be preferably 330 µm or less, particularly preferably 220 µm or less, and further preferably 160 µm or less. The thickness of the cover film for testing 1 being 30.5 µm or more allows the cover film for testing 1 to have sufficient strength to improve the handling ability and it is possible to suppress the deformation and breakage of the cover film for testing 1 when the testing member 100 is used. The thickness of the cover film for testing 1 being 330 µm or less allows the cover film for testing 1 to readily have excellent transparency to the testing light and the test may be well performed in the obtained testing member 100.

3. Method of Manufacturing Cover Film for Testing

The method of manufacturing the cover film for testing 1 according to the present embodiment is not particularly limited. Examples of the method include a method of coating one surface of the base material 10 with a coating liquid that contains a material for constituting the thermoplastic resin layer 20 and drying the coating liquid to form the thermoplastic resin layer 20, a method of laminating a material for constituting the thermoplastic resin layer 20 on one surface of the base material 10 by extrusion lamination, and a method of coextrusion molding of a material for constituting the base material 10 and a material for constituting the thermoplastic resin layer 20.

Examples of the method of coating one surface of the base material 10 with a coating liquid that contains a material for constituting the thermoplastic resin layer 20 and drying the coating liquid to form the thermoplastic resin layer 20 include a method of preparing a coating liquid that contains a material for constituting the thermoplastic resin layer 20 and if necessary further contains some solvent or dispersant, coating one surface of the base material 10 with the coating liquid to form a coating film using a coater, such as a die coater, curtain coater, spray coater, slit coater, and knife coater, and drying the coating film.

Examples of the method of manufacturing the cover film for testing 1 through laminating the thermoplastic resin layer 20 on the base material 10 by extrusion lamination include a method of obtaining the cover film for testing 1 through melting and kneading a material for constituting the thermoplastic resin layer 20 using a T-die film formation machine or the like and laminating the above molten material on one surface of the base material 10 by extrusion lamination while moving the base material 10 at a constant speed. The temperature for melting the material for constituting the thermoplastic resin layer 20 is preferably a temperature to such an extent that the base material 10 does not deform due to the temperature (heat) of the molten material and, for example, may be preferably 120° C. or higher and particularly preferably 150° C. or higher. The temperature may be preferably 300° C. or lower and particularly preferably 250° C. or lower.

<Testing Member>

FIG. 2 illustrates a cross-sectional view of the testing member 100 according to the present embodiment. The testing member 100 comprises a substrate 2 having a surface provided with at least one groove 4 and the cover film for testing 1 according to the present embodiment laminated on the surface of the substrate 2 provided with the grooves 4.

The testing member 100 according to the present embodiment may be for performing an optical test for a specimen stored in each groove 4.

In the testing member 100 according to the present embodiment, the cover film for testing 1 and the substrate 2 are well fixed to each other via the thermoplastic resin layer 20 of the cover film for testing 1. In the testing member 100, therefore, the use of a pressure sensitive adhesive is not necessary for fixation between the cover film for testing 1 and the substrate 2 and there is no possibility that such a pressure sensitive adhesive invades into or fills the grooves 4. Moreover, the thermoplastic resin which constitutes the thermoplastic resin layer 20 has high elasticity even when heated as compared with a pressure sensitive adhesive and, therefore, the thermoplastic resin can be suppressed from invading into the grooves 4 of the substrate 2 when the cover film for testing 1 and the substrate 2 are fixed by thermal fusion bonding of the thermoplastic resin layer 20. As the above, according to the testing member 100 of the present embodiment, the test can be well performed.

The shape in the plan view of the testing member 100 according to the present embodiment is not particularly restricted, but may preferably be a disk-like shape or chip-like shape. The disk-like shape refers to a precisely circular shape or its modified shape in the plan view of the testing member 100. In the case of such a disk-like shape, a hole may be provided at the center of the testing member 100. The shape of the hole may be a circular shape that is concentric in the plan view with the circumference of the testing member 100. The chip-like shape refers to a square shape, rectangular shape, or their modified shapes in the plan view of the testing member 100.

1. Configuration of Testing Member
(1) Substrate

In the testing member 100 according to the present embodiment, the substrate 2 is not particularly limited, provided that the test can be performed using the testing member 100 which includes the substrate 2. From the viewpoint of enabling a good test, it may be preferred for the substrate 2 to have transparency to the testing light.

As a material of the substrate 2, a resin, glass, and other appropriate material can be used, among which the resin may preferably be used from the viewpoint of easy production and easy handling. As the resin, resins that constitute the previously-described resin films can be used as in the base material 10. Among such resins, polycarbonate, polyethylene terephthalate, or acrylic-based resin may preferably be used and the polycarbonate may be particularly preferably used from the viewpoint of excellent transparency to the testing light and excellent moldability. As previously described, the same material as that of the base material 10 may preferably be used as a material of the substrate 2 from the viewpoint of reducing the difference in the transparency to the testing light.

The glass-transition temperature (Tg) of the material which constitutes the substrate 2 may be preferably 100° C. or higher, particularly preferably 120° C. or higher, and further preferably 140° C. or higher. When the above glass-transition temperature (Tg) is 100° C. or higher, the substrate 2 does not readily melt even if the testing member 100 is heated during the test. It is therefore possible to effectively suppress the deformation of the substrate 2 and to effectively suppress the occurrence of delamination and/or displacement at the interface between the thermoplastic resin layer 20 and the substrate 2. The upper limit of the glass-transition temperature (Tg) of the material which constitutes the substrate 2 is not particularly restricted, but in general may be preferably 300° C. or lower, particularly preferably 250° C. or lower, and further preferably 200° C. or lower.

In the testing member 100 according to the present embodiment, the transmittance of the testing light through the substrate 2 may be preferably 60% or higher, particularly preferably 80% or higher, and further preferably 90% or higher. The above transmittance being 60% or higher allows the testing member 100 to have better transparency to the testing light and the test can be more accurately performed. The upper limit of the above transmittance is not particularly limited and may be 100% or lower.

In the testing member 100 according to the present embodiment, the haze value of the substrate 2 may be preferably 10% or less, particularly preferably 5% or less, and further preferably 1% or less. The haze value of the substrate 2 being 10% or less can effectively reduce the scattering of the testing light in the substrate 2. In the testing member 100, therefore, the test can be more accurately performed. The lower limit of the haze value of the substrate 2 is not particularly limited, but may ordinarily be 0% or more.

One surface of the substrate 2 is provided with at least one groove 4. In the substrate 2 of the testing member 100 illustrated in FIG. 2, the surface of the substrate 2 at the thermoplastic resin layer 20 side is provided with a plurality of grooves 4 (three grooves 4 in FIG. 2) that each have a width w1 and depth d1.

The cross-sectional shape of each groove 4 is not limited, provided that the groove 4 can store a specimen and the test can be well performed. In FIG. 2, the shape of the cross section is a triangle, but is not limited to this. In an alternative embodiment, the shape of the cross section may be a square, rectangle, semicircle, or other appropriate shape.

The shape in the plan view of each groove 4 is also not limited, provided that the groove 4 can store a specimen and the test can be well performed. For example, the shape may be a line-like shape, dot-like shape, or other appropriate shape. From the viewpoint that the testing light can be scanned along the groove 4, the shape may preferably be a line-like shape. In the case of the line-like shape, the shape in the plan view of the groove 4 may preferably be a linear shape or curved shape. When the testing member 100 is in the previously-described disk-like shape, the groove 4 may preferably be arranged in a circular shape that is concentric in the plan view with the outer circumference of the testing member 100. In this case, scanning of the testing light for the groove 4 can be easily performed by rotating the testing member 100 around an axis of rotation, that is, a straight line that passes through the center of the circular shape and is orthogonal to the circular shape.

Surface treatment for improving the wettability may preferably be performed for the surface of the substrate 2 at the cover film for testing 1 side, in particular, for portions of the surface that constitute the grooves 4. This allows a specimen to be well stored in each groove 4 because the specimen wets the groove 4 and spreads along the groove 4 when the specimen is stored in the groove 4. Examples of the above surface treatment include a method of coating the objected surface with a component that improves the wettability and a method of performing surface modification. Examples of the component which improves the wettability include components for hydrophilic coating. Examples of the scheme of surface modification include corona treatment, plasma treatment, ultraviolet ray treatment, and flame treatment.

With regard to the above wettability, the surface tension on the surface of the substrate 2 at the cover film for testing 1 side may be preferably 30 mN/m or more, particularly preferably 35 mN/m or more, and further preferably 40 mN/m or more. The surface tension being 30 mN/m or more allows the specimen to be well stored in each groove 4 because the specimen wets the groove 4 and spreads along the groove 4 when the specimen is stored in the groove 4. As a result, the test may be well performed. The upper limit of the surface tension is not particularly limited, but in general may be preferably 70 mN/m or less, particularly preferably 65 mN/m or less, and further preferably 60 mN/m or less. The surface tension refers to a value that is measured by a wetting tension test in accordance with JIS K6768: 1990.

In the testing member 100 according to the present embodiment, dimensions of each groove 4 can be set in accordance with the method of testing to be performed and the type of the specimen. For example, the width w1 of the groove 4 may be preferably 50 nm or more, particularly preferably 100 nm or more, and further preferably 150 nm or more. The width w1 may be preferably 30 µm or less, particularly preferably 10 µm or less, and further preferably 1 µm or less. The depth d1 of the groove 4 may be preferably 50 nm or more, particularly preferably 100 nm or more, and further preferably 150 nm or more. The depth d1 may be preferably 30 µm or less, particularly preferably 10 µm or less, and further preferably 1 µm or less. The width w1 and depth d1 of each groove 4 being within the above ranges can sufficiently ensure the length along which the testing light transmits through the specimen, while suppressing the necessary amount of the specimen.

In the testing member 100 according to the present embodiment, the arithmetic average roughness (Ra) of the surface of the substrate 2 opposite to the surface formed with the grooves 4 may be preferably 200 nm or less, particularly preferably 100 nm or less, and further preferably 50 nm or less. The arithmetic average roughness (Ra) being 200 nm or less can suppress the diffuse reflection of the testing light at the surface of the testing member 100 at the substrate 2 side and the testing member 100 may readily have excellent transparency to the testing light to improve the accuracy in the test. The lower limit of the above arithmetic average roughness (Ra) is not particularly limited, but in general may be preferably 0.1 nm or more, particularly preferably 0.5 nm or more, and further preferably 1 nm or more. The above arithmetic average roughness (Ra) can be obtained by applying the method of measuring the arithmetic average roughness Ra as described in the exemplary test, which will be described later, to the surface of the substrate 2 opposite to the surface formed with the grooves 4.

In the testing member 100 according to the present embodiment, the thickness of the substrate 2 (distance between the surface laminated with the thermoplastic resin layer 20 and the opposite surface) may be preferably 0.5 mm or more, particularly preferably 0.8 mm or more, and further preferably 1 mm or more. The thickness may be preferably 10 mm or less, particularly preferably 5 mm or less, and further preferably 3 mm or less. The thickness of the substrate 2 being 0.5 mm or more allows the substrate 2 to have sufficient strength and it is possible to effectively suppress the deformation of the testing member 100 when it stores the specimen and is used for the test. The thickness of the substrate 2 being 10 mm or less allows the testing light to readily arrive at the specimen during the test and the test may be accurately performed.

(2) Others

The testing member 100 according to the present embodiment may be provided with an opening part for storing the specimen in each groove 4. The opening part may be provided at at least one of the cover film for testing 1 and the substrate 2, but in particular may preferably be provided at the cover film for testing 1. With regard to the shape and size of the opening part, the opening part may preferably be formed in a shape that is suitable for a storing means used for storing the specimen in the groove 4. A syringe, pipette, or other appropriate instrument may be used as the storing means. When a syringe is used, for example, the opening part may preferably have a shape and size that allow the tip of an injection needle of the syringe to reach the groove 4. As will be understood, when the testing member 100 according to the present embodiment is provided with the above opening part, it is preferred to provide an air-bleeding hole.

2. Physical Properties of Testing Member

The testing member 100 according to the present embodiment may preferably satisfy at least one of Expressions (1) and (2) below:

$$Tg_1 > Tg_2 \quad (1)$$

$$Tg_3 > Tg_2 \quad (2)$$

where $Tg_1$ represents the glass-transition temperature of a material that constitutes the base material 10, $Tg_2$ represents the glass-transition temperature of a thermoplastic resin that constitutes the thermoplastic resin layer 20, and $Tg_3$ represents the glass-transition temperature of a material that constitutes the substrate 2.

Satisfaction of at least one of the above Expressions (1) and (2) can effectively suppress the deformation due to heat of at least one of the base material 10 and the substrate 2 when, for the production of the testing member 100, the cover film for testing 1 and the substrate 2 are fixed to each other by thermal fusion bonding of the thermoplastic resin layer 20. In particular, the testing member 100 according to the present embodiment may preferably satisfy both the above Expressions (1) and (2) from the viewpoint of effectively suppressing the deformation due to heat of both the base material 10 and the substrate 2.

3. Method of Manufacturing Testing Member

The testing member 100 according to the present embodiment can be manufactured through attaching the surface of the previously-described cover film for testing 1 at the thermoplastic resin layer 20 side and the surface of the substrate 2 at the side formed with the grooves 4 to each other by thermal fusion bonding of the thermoplastic resin layer 20. In particular, the method of manufacturing the testing member 100 preferably includes a step of performing thermal fusion bonding between the surface of the substrate 2 provided with the grooves 4 and the surface of the cover film for testing 1 at the thermoplastic resin layer 20 side so that the substrate 2 and the cover film for testing 1 adhere to each other. In this method, the thermal fusion bonding is performed without filling the grooves 4 with the thermoplastic resin layer 20. In this case, the specific scheme is not limited, provided that the thermoplastic resin layer 20 in a state of being heated to melt can be laminated on the substrate 2. For example, this lamination can be performed, such as by thermal lamination and thermocompression. In particular, the thermal lamination may preferably be performed from the viewpoint of effectively suppressing the molten thermoplastic resin layer 20 from invading into the grooves 4 and effectively suppressing the deformation due to heat of the grooves 4 and also from the viewpoint of simplicity.

Conditions of the thermal lamination are not particularly limited, provided that the cover film for testing 1 and the substrate 2 can be well fixed to each other and the thermoplastic resin which constitutes the thermoplastic resin layer 20 is suppressed from invading into the grooves 4 of the substrate 2. For example, the thermal lamination can be performed using heating rollers and the heating temperature may be preferably 60° C. or higher and particularly preferably 80° C. or higher. The heating temperature may be preferably 150° C. or lower and particularly preferably 120° C. or lower. The pressure for lamination may be preferably 0.1 MPa or more and particularly preferably 0.5 MPa or more. The pressure may be preferably 10 MPa or less and particularly preferably 5 MPa or less. The speed of lamination may be preferably 0.1 m/min or more and particularly preferably 0.5 m/min or more. The speed of lamination may be preferably 5 m/min or less and particularly preferably 1 m/min or less. When the thermal lamination is performed under such a heating temperature, pressure, and speed, the thermoplastic resin can be effectively suppressed from invading into the grooves 4, and the cover film for testing 1 and the substrate 2 can be well fixed to each other. In particular, the heating temperature within the above range allows the thermal lamination to be performed at a temperature that is lower than the glass-transition temperatures of the base material 10 and the substrate 2. The deformation due to heat of the base material 10 and the substrate 2 can therefore be prevented and the testing member 100 can be obtained with which a good test is possible.

Conditions of the thermocompression are not particularly limited, provided that the cover film for testing 1 and the substrate 2 can be well fixed to each other and the thermoplastic resin which constitutes the thermoplastic resin layer 20 is suppressed from invading into the grooves 4 of the substrate 2. For example, the thermocompression can be performed using a thermal pressing machine and the heating temperature may be preferably 60° C. or higher and particularly preferably 70° C. or higher. The heating temperature may be preferably 150° C. or lower and particularly preferably 140° C. or lower. The pressure for thermocompression may be preferably 0.1 MPa or more and particularly preferably 0.5 MPa or more. The pressure may be preferably 20 MPa or less and particularly preferably 10 MPa or less. The time of thermocompression may be preferably 1 minute or more and particularly preferably 5 minutes or more. The time of thermocompression may be preferably 20 minutes or less and particularly preferably 15 minutes or less. When the thermocompression is performed under such conditions, the thermoplastic resin can be effectively suppressed from invading into the grooves 4, and the cover film for testing 1 and the substrate 2 can be well fixed to each other. In particular, the heating temperature within the above range allows the thermocompression to be performed at a temperature that is lower than the glass-transition temperatures of the base material 10 and the substrate 2. The deformation due to heat of the base material 10 and the substrate 2 can therefore be prevented and the testing member 100 can be obtained with which a good test is possible.

The method of manufacturing the substrate 2 is not particularly limited. When the substrate 2 is formed of a resin, the substrate 2 may preferably be manufactured through molding the substrate 2, such as by injection molding, compression molding and insertion molding, and if necessary performing other processing, such as surface processing.

4. Method of Using Testing Member

The testing member 100 according to the present embodiment can be used for an optical test for a specimen. Specifically, after a specimen is stored in each groove 4 of the testing member 100, the stored specimen may be irradiated with light from outside of the testing member 100 and the light caused by the irradiation may be measured outside the testing member 100.

The specimen may preferably have flowability from the viewpoint that the specimen can readily be stored in each groove 4. Examples of the specimen include a liquid, sol-like component, and gel-like component. In particular, the specimen may preferably be a liquid. The liquid may contain a solid component. Specific examples of the specimen include water as an object of a water quality test, cell extract, blood, cultured cell liquid, bacteria, archaebacteria, virus, protein, algae, and microbe.

The specimen can be stored in each groove 4 through supplying the specimen into the groove 4 via the opening part provided at the testing member 100, for example, using the previously-described storing means. In an embodiment, a syringe or the like provided with an injection needle may be used to operate the injection needle to penetrate at a certain position of the testing member 100 and the specimen may then be supplied into the groove 4 via the syringe.

Irradiation of the stored specimen with the testing light and the subsequent measurement may be selected in accordance with the purpose of the test. For example, when measuring the concentration of a component that absorbs light of a certain wavelength, the absorbance at the wavelength may be measured. Specifically, the specimen is irradiated with the testing light which includes light of the wavelength, and the amount of light of the wavelength included in the light which transmits through the specimen may then be measured. On the basis of the absorbance thus obtained, the amount of the above component in the specimen can be estimated. In the case of a test for the turbidity of the specimen, scattering light is detected which is generated when the testing light with which the specimen is irradiated encounters particles included in the specimen and, on the basis thereof, the degree of turbidity due to the particles can be estimated. In the case of a test for an activity state, as an index of the state of cells or blood, of a fluorescent component in the specimen which contains the cells or blood, a desired test can be performed through irradiating the specimen with the testing light which includes exciting light and measuring the fluorescence which is emitted from the fluorescent component due to the irradiation.

The type of testing light can be selected in accordance with the purpose of the test. The testing light may be, for example, laser light. In this case, the wavelength of the testing light may be preferably 200 nm or more and particularly preferably 400 nm or more. The wavelength may be preferably 1,000 nm or less and particularly preferably 800 nm or less. In particular, it may be preferred to use Ar laser (wavelength: 488 to 514 nm) or He—Ne laser (wavelength: 630 nm) as the testing light.

When the testing member 100 is used, the testing member 100 may be cooled or heated in accordance with the specimen to be used and the test to be performed. When the testing member 100 is heated, however, it may be preferred to perform the heating up to a temperature lower than the melting point of each material that constitutes the testing member 100, from the viewpoint of suppressing the deformation due to heat of the testing member 100.

It should be appreciated that the embodiments heretofore explained are described to facilitate understanding of the present invention and are not described to limit the present invention. It is therefore intended that the elements disclosed in the above embodiments include all design changes and equivalents to fall within the technical scope of the present invention.

For example, the thermoplastic resin layer 20 may be laminated on a partial region of one surface of the base material 10, provided that the base material 10 and the substrate 2 can be attached to each other. In this case, for example, the testing member 100 may be configured such that the thermoplastic resin layer 20 is not laminated on a region that overlaps with the grooves 4 in the plan view, but is laminated on a region other than the overlapping region.

EXAMPLES

Hereinafter, the present invention will be described further specifically with reference to examples, etc., but the scope of the present invention is not limited to these examples, etc.

Example 1

(1) Production of Substrate

A substrate having three grooves on one surface (see the substrate 2 of FIG. 2) was formed through injection molding of a polycarbonate resin (product name "Panlite AD-5503" available from TEIJIN LIMITED, Tg: 145° C.). The substrate has a disk-like shape of a diameter of 12 cm and a thickness of 1.2 mm, and a circular hole having a diameter of 1.5 cm is provided at the center in the plan view to be concentric with the outer circumference. The three grooves are provided at an interval of 0.25 mm to be concentric with the outer circumference of the substrate in the plan view, and the width w1 and depth d1 of each groove are 200 nm. The distance between the groove nearest to the outer circumference of the substrate and the outer circumference of the substrate is 2 cm. As a result of measurement, the arithmetic average roughness (Ra) of the surface of the substrate opposite to the surface formed with the grooves was 120 nm, the transmittance of the testing light (wavelength: 0.63 μm) was 92%, and the haze value was 0.1%.

(2) Production of Cover Film for Testing

A coaling liquid of a thermoplastic resin composition having a solid content concentration of about 15 mass % was prepared through mixing 100 mass parts of a polyester resin as the thermoplastic resin (product name "Vylonal MD-1245" available from TOYOBO CO., LTD., weight-average molecular weight: 20,000, Tg: 61° C.), 40 mass parts of water, and 60 mass parts of isopropyl alcohol. One surface of a polycarbonate film as the base material (product name "PURE-ACE" available from TEIJIN LIMITED, thickness: 100 μm, arithmetic average roughness (Ra) of surface opposite to surface to be formed with thermoplastic resin layer: 150 nm, transmittance of testing light (wavelength: 0.63 μm): 90% or more, haze value: 0.3% or less, Tg: 160° C.) was coated with the prepared coating liquid of the thermoplastic resin composition using a Meyer bar and the obtained coating film was dried at 120° C. for one minute to obtain a laminate in which a thermoplastic resin layer having a thickness of 1 μm was laminated on the one surface of the base material.

The obtained laminate was cut into the same shape in the plan view as that of the substrate produced in the process (1). Specifically, the laminate was cut into a disk-like shape of a diameter of 12 cm with its center provided with a circular hole of a diameter of 1.5 cm concentric with the outer circumference. A cover film for testing was thus obtained.

(3) Production of Testing Member

Subsequently, the surface formed with the grooves of the substrate produced in the process (1) and the surface at the thermoplastic resin layer side of the cover film for testing produced in the process (2) were attached to each other through performing thermocompression under a heating temperature of 140° C. and a pressure of 1 MPa for 10 minutes using a thermal pressing machine. A testing member was thus manufactured.

Example 2

A coaling liquid of a thermoplastic resin composition was prepared through mixing 100 mass parts of a polyester resin as the thermoplastic resin (product name "Vylonal MD-1100" available from TOYOBO CO., LTD., weight-average molecular weight: 20,000, Tg: 40° C.), 40 mass parts of water, and 60 mass parts of isopropyl alcohol and diluting the mixture to a solid content concentration of about 15 mass %.

A testing member was manufactured in the same manner as in Example 1 except that the coating liquid of the thermoplastic resin composition prepared as the above was used and, in the production of the testing member, the surface formed with the grooves of the substrate and the surface at the thermoplastic resin layer side of the cover film for testing were attached to each other through performing thermal lamination under a heating temperature of 100° C., a pressure of 0.5 MPa, and a speed of 0.5 m/min using heating rollers.

Comparative Example 1

(1) Production of Cover Film for Testing

A polycarbonate film (product name "PURE-ACE" available from TEIJIN LIMITED, thickness: 100 μm, arithmetic average roughness (Ra) of surface opposite to surface to be attached to substrate: 150 nm, transmittance of testing light (wavelength: 0.63 μm): 90% or more, haze value: 0.3% or less, Tg: 160° C.) was cut into the same shape in the plan view as that of the substrate produced in the process (1) of Example 1. Specifically, the polycarbonate film was cut into a disk-like shape of a diameter of 12 cm with its center provided with a circular hole of a diameter of 1.5 cm concentric with the outer circumference. A cover film for testing was thus obtained.

(2) Production of Testing Member

Subsequently, the surface formed with the grooves of the substrate produced in the process (1) of Example 1 and the cover film for testing produced in the above process (1) were attached to each other through performing thermocompression under a heating temperature of 250° C. and a pressure of 1 MPa for 1 minutes using a thermal pressing machine. A testing member was thus manufactured.

Comparative Example 2

(1) Preparation of Pressure Sensitive Adhesive Composition

An acrylic ester copolymer was prepared through copolymerization of 20 mass parts of 2-ethylhexyl acrylate, 75 mass parts of butyl acrylate, and 5 mass parts of 4-hydroxybutyl acrylate. When the molecular weight of the acrylic ester copolymer was measured using the method to be described later, the weight-average molecular weight (Mw) was 200,000.

A coating liquid of a pressure sensitive adhesive composition having a solid content concentration of 28 mass % was prepared through uniformly mixing 100 mass parts (solid content equivalent, here and hereinafter) of the above acrylic ester copolymer, 6 mass parts of hexamethylene diisocyanate-based isocyanurate as a crosslinker (product name "CORONATE HX" available from NIPPON POLYURETHANE INDUSTRY CO., LTD.), and methyl ethyl ketone as a diluting solvent.

Here, the previously-described weight-average molecular weight (Mw) refers to a weight-average molecular weight that is measured as a standard polystyrene equivalent value under the following condition using gel permeation chromatography (GPC) (GPC measurement).

<Measurement Condition>
- GPC measurement apparatus: HLC-8020 available from Tosoh Corporation
- GPC columns (passing in the order below) available from Tosoh Corporation
  - TSK guard column HXL-H
  - TSK gel GMHXL (×2)
  - TSK gel G2000HXL
- Solvent for measurement: tetrahydrofuran
- Measurement temperature: 40° C.

(2) Formation of Pressure Sensitive Adhesive Layer

The release surface of a release sheet obtained by forming a silicone-based release agent layer on one surface of a polyethylene terephthalate film having a thickness of 38 μm ("SP-PET381031" available from LINTEC Corporation) was coated with the coating liquid of the pressure sensitive adhesive composition prepared in the process (1) using a comma coater and the obtained coating film was dried in an oven of 90° C. for one minute to form a pressure sensitive adhesive layer having a thickness of 3 μm. A release sheet with pressure sensitive adhesive layer was thus obtained.

The surface at the pressure sensitive adhesive layer side of the obtained release sheet with pressure sensitive adhesive layer and one surface of a polycarbonate film as the base material (product name "PURE-ACE" available from TEIJIN LIMITED, thickness: 100 μm, arithmetic average roughness (Ra) of surface opposite to surface to be formed with pressure sensitive adhesive layer: 150 nm, transmittance of testing light (wavelength: 0.63 μm): 90% or more, haze value: 0.3% or less, Tg: 160° C.) were attached to each other and a laminate was obtained in which the base material, the pressure sensitive adhesive layer, and the release sheet were laminated in this order.

Thereafter, the obtained laminate was cut into the same shape in the plan view as that of the substrate produced in the process (1) of Example 1. Specifically, the laminate was cut into a disk-like shape of a diameter of 12 cm with its center provided with a circular hole of a diameter of 1.5 cm concentric with the outer circumference. A cover film for testing was thus obtained.

(3) Production of Testing Member

Subsequently, the surface formed with the grooves of the substrate produced in the process (1) and the surface at the pressure sensitive adhesive layer side of the cover film for testing produced in the process (2) were attached to each other through performing lamination under a temperature of 25° C., a pressure of 0.5 MPa, and a speed of 0.5 m/min. A testing member was thus manufactured.

<Exemplary Test 1> (Evaluation of Interfacial Adhesion)

For the testing member manufactured in each of the examples and comparative examples, the interfacial adhesion was evaluated in accordance with the criteria below through pressing a finger against the cover film for testing with the substrate fixed and applying force in a planar direction.

○: Dislocation did not occur at the interface between the substrate and the cover film for testing.

x: Dislocation did occur at the interface between the substrate and the cover film for testing.

<Exemplary Test 2> (Evaluation of Invasion into Grooves)

The cross section of a groove of the testing member manufactured in each of the examples and comparative examples was observed using an electron microscope (product name "VE-9800" available from KEYENCE CORPORATION) and evaluation was performed in accordance with the criteria below for the invasion into the groove of the thermoplastic resin constituting the thermoplastic resin layer or the invasion into the groove of the pressure sensitive adhesive constituting the pressure sensitive adhesive layer.

○: Invasion was less than 20% of the cross section of the groove.

x: Invasion was 20% or more of the cross section of the groove.

<Exemplary Test 3> (Evaluation of Deformation of Grooves)

Cross sections of grooves of the testing member manufactured in each of the examples and comparative examples were observed using an electron microscope (product name "VE-9800" available from KEYENCE CORPORATION) and deformation of the grooves was evaluated in accordance with the criteria below.

○: Deformation of the grooves did not occur.

x: Deformation of the grooves did occur.

TABLE 1

| | Presence or absence of thermoplastic resin layer | Glass-transition temperature (Tg) (° C.) of thermoplastic resin | Attaching of cover film for testing and substrate | | Evaluation of interfacial adhesion | Evaluation of invasion into grooves | Evaluation of deformation of grooves |
|---|---|---|---|---|---|---|---|
| | | | Method | Temperature (° C.) | | | |
| Example 1 | Present | 61 | Thermocompression | 140 | ○ | ○ | ○ |
| Example 2 | Present | 40 | Thermal lamination | 100 | ○ | ○ | ○ |
| Comparative Example 1 | Absent | — | Thermocompression | 250 | ○ | — | x |
| Comparative Example 2 | Absent (but pressure sensitive adhesive layer is provided) | — | Lamination | 25 | ○ | x | ○ |

As apparent from Table 1, in the testing member produced in each of Examples 1 and 2, the thermoplastic resin does not invade into the grooves and deformation of the grooves does not occur.

INDUSTRIAL APPLICABILITY

The cover film for testing and the testing member according to the present invention are suitable for a method of optically measuring a slight amount of a specimen.

DESCRIPTION OF REFERENCE NUMERALS

1 . . . Cover film for testing
  10 . . . Base material
  20 . . . Thermoplastic resin layer
100 . . . Testing member
  2 . . . Substrate
  4 . . . Groove

The invention claimed is:

1. A testing member comprising:
a substrate having a surface provided with at least one groove configured to store a specimen; and
a cover film laminated on the surface of the substrate provided with the at least one groove by thermal lamination or thermocompression carried out at temperatures, pressures, and time periods effective for suppressing a thermoplastic resin from invading into the at least one groove provided on the surface of the substrate, wherein
the cover film being a cover film for testing comprising a base material that includes a top surface and a bottom surface on an opposite side of the top surface; and the thermoplastic resin layer laminated on the bottom surface of the base material and completely covering the bottom surface of the base material,
the cover film for testing satisfies Expression (1) below:

$$Tg_1 > Tg_2 \quad (1)$$

where $Tg_1$ represents a glass-transition temperature of a material that constitutes the base material and $Tg_2$ represents a glass-transition temperature of a thermoplastic resin that constitutes the thermoplastic resin layer, and
the testing member being configured for performing an optical test on the specimen stored in the at least one groove.

2. The testing member as recited in claim 1, wherein the thermoplastic resin that constitutes the thermoplastic resin layer has the $Tg_2$ of 35° C. or higher and 150° C. or lower.

3. The testing member as recited in claim 2, wherein the cover film for testing has a thickness of 30.5 μm or more and 330 μm or less.

4. The testing member as recited in claim 3, wherein the cover film for testing has transparency to light used in the test.

5. The testing member as recited in claim 1, wherein the cover film for testing has transparency to light used in the test.

6. The testing member as recited in claim 1, wherein the thermoplastic resin layer has a thickness of 0.5 μm or more and 30 μm or less.

7. The testing member as recited in claim 1 wherein,
the testing member satisfies Expression (2) below:

$$Tg_3 > Tg_2 \quad (2)$$

where $Tg_3$ represents the glass-transition temperature of a material that constitutes the substrate.

\* \* \* \* \*